United States Patent
Grodzins et al.

(10) Patent No.: US 6,320,933 B1
(45) Date of Patent: Nov. 20, 2001

(54) MULTIPLE SCATTER SYSTEM FOR THREAT IDENTIFICATION

(75) Inventors: Lee Grodzins, Lexington, MA (US); William Adams, Powell, OH (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

(21) Appl. No.: 09/448,721

(22) Filed: Nov. 24, 1999

Related U.S. Application Data

(60) Provisional application No. 60/110,185, filed on Nov. 30, 1998.

(51) Int. Cl.[7] ................................................. G01B 15/02
(52) U.S. Cl. .................................................. 378/89; 378/86
(58) Field of Search ........................................ 378/86, 89

(56) References Cited

U.S. PATENT DOCUMENTS

| | | | |
|---|---|---|---|
| 3,961,186 | 6/1976 | Leunbach | 250/272 |
| 4,380,817 | 4/1983 | Harding et al. | 378/87 |
| 4,525,854 * | 7/1985 | Molbert et al. | 378/89 |
| 4,864,142 | 9/1989 | Gomberg | 250/390.04 |
| 5,430,787 | 7/1995 | Norton | 378/87 |
| 5,763,886 | 6/1998 | Schulte | 250/358.1 |

FOREIGN PATENT DOCUMENTS

| | | | |
|---|---|---|---|
| 0 864 884 A2 | 4/1998 | (EP) | G01V/5/12 |
| WO 98/20366 | 7/1997 | (WO) | G01T/1/29 |

* cited by examiner

*Primary Examiner*—Craig E. Church
(74) *Attorney, Agent, or Firm*—Bromberg & Sunstein LLP

(57) ABSTRACT

A system and a method for determining the density of an object. The intensity of x-rays backscattered from the object is measured by at least two backscatter detectors disposed at different distances from the intersection of an incident x-ray beam with the plane of the detectors. At least one of detectors is sensitive only to x-rays that have scattered more than once in the object, the ratio of scattered x-rays measured by the detectors being a function of the density of the scattering medium.

10 Claims, 3 Drawing Sheets

MULTIPLE SCATTER SYSTEM FOR THREAT IDENTIFICATION

The present application claims priority from U.S. Provisional Application No. 60/110,185, filed Nov. 30, 1998, which is incorporated herein by reference.

TECHNICAL FIELD

The present invention relates to x-ray inspection of containers or of the ground, and, more particularly, to x-ray inspection employing the detection of backscatter radiation by means of multiple backscatter detectors in order to derive information including both density and effective atomic number with respect to sources of scattering.

BACKGROUND OF THE INVENTION

It is desirable to be able to determine the presence of objects, such as contraband, weapons, or explosives, that have been concealed in an enclosure, such as luggage or a shipping container. Conventional x-ray techniques provide measures either of attenuation, in the case of transmission techniques, or of scatter, in the case of scatter techniques.

The measurement of the intensity of x-rays backscattered from an object has been used extensively to give a measure of the effective atomic number of the object. Various methods of identifying a backscatter signal with a position within the illuminated object employ scanned pencil beams of x-rays, as described, for example, in U.S. Pat. Nos. 4,809,312 and 4,825,454 which are hereby incorporated herein by reference. In practice, the backscatter intensity may give only a crude measure of the atomic number of the object since the backscatter intensity is a function of several variables: the effective atomic number of the object; the object's geometry, including its distance from the x-ray source and the detectors; and the presence of material interposed between the object and the x-ray source/detector arrangement. In particular, current backscatter techniques do not provide a measure of the density of the scattering object.

SUMMARY OF THE INVENTION

In accordance with one aspect of the invention, in a preferred embodiment, there is provided an inspection system for analyzing the density of an object which may be concealed within an enveloping surface. The system has a source of penetrating radiation for emitting a beam having a propagation axis, the beam being incident upon the object. The system has a first scatter detector for detecting penetrating radiation scattered at least one time within the object and for generating a first signal, and, additionally, a second scatter detector, having a field of view, for generating a second signal corresponding to penetrating radiation that has been multiply scattered within the object. Furthermore, the system has a controller for determining an effective density of the object on the basis of at least the first and second signals. In accordance with alternate embodiments of the invention, the first scatter detector may be disposed at a first distance measured on an orthogonal to the propagation axis of the beam and the second scatter detector may disposed at a second distance measured on an orthogonal to the propagation axis of the beam, the second distance being greater than the first distance.

The field of view of the second scatter detector may be limited by at least one collimator to radiation that has been multiply scattered within the object, and the second scatter detector may also be limited by spectral sensitivity from detecting penetrating radiation scattered fewer than twice by the object.

In accordance with a further alternate embodiment of the invention, the system may have a third scatter detector for generating a third signal corresponding to penetrating radiation that has been multiply scattered within the object, such that the controller determines an effective density of the object on the basis of the first, second, and third signals. The source of penetrating radiation may be an x-ray source, and, more particularly, a radioactive x-ray source. The system may also have a scanner for moving the propagation axis of the beam of penetrating radiation relative to the object.

In accordance with further aspects of the present invention, in other embodiments, there are provided methods for analyzing an object concealed within the ground or within an enclosure. The methods have the steps of illuminating the ground or the enclosure with a beam of penetrating radiation, generating a first signal corresponding to penetrating radiation scattered at least one time within the object, generating a second signal corresponding to penetrating radiation that has been multiply scattered within the object, and determining an effective density of the object on the basis of at least the first and second signals.

BRIEF DESCRIPTION OF THE DRAWINGS

The foregoing features of the invention will be more readily understood by reference to the following detailed description taken with the accompanying drawings in which.

DETAILED DESCRIPTION OF PREFERRED EMBODIMENTS

A principle of operation of a preferred embodiment of the present invention, whereby the density of an object may be derived by measuring the intensity of x-rays backscattered from the object, is described with reference to FIG. 1. A beam 10 of penetrating radiation is incident upon an object 13 which may be concealed from view, such as by enclosure within container 11. 'Penetrating radiation' refers to electromagnetic radiation of an appropriate range of energy and intensity as to penetrate container 11 and object 13, and will be referred to, without limitation, in the following description as x-ray radiation. Beam 10 will similarly be referred to, without limitation, as an x-ray beam. Beam 10 is generated by source 8 of penetrating radiation which may, for example, be an x-ray tube or a radioactive source.

Figure 1:
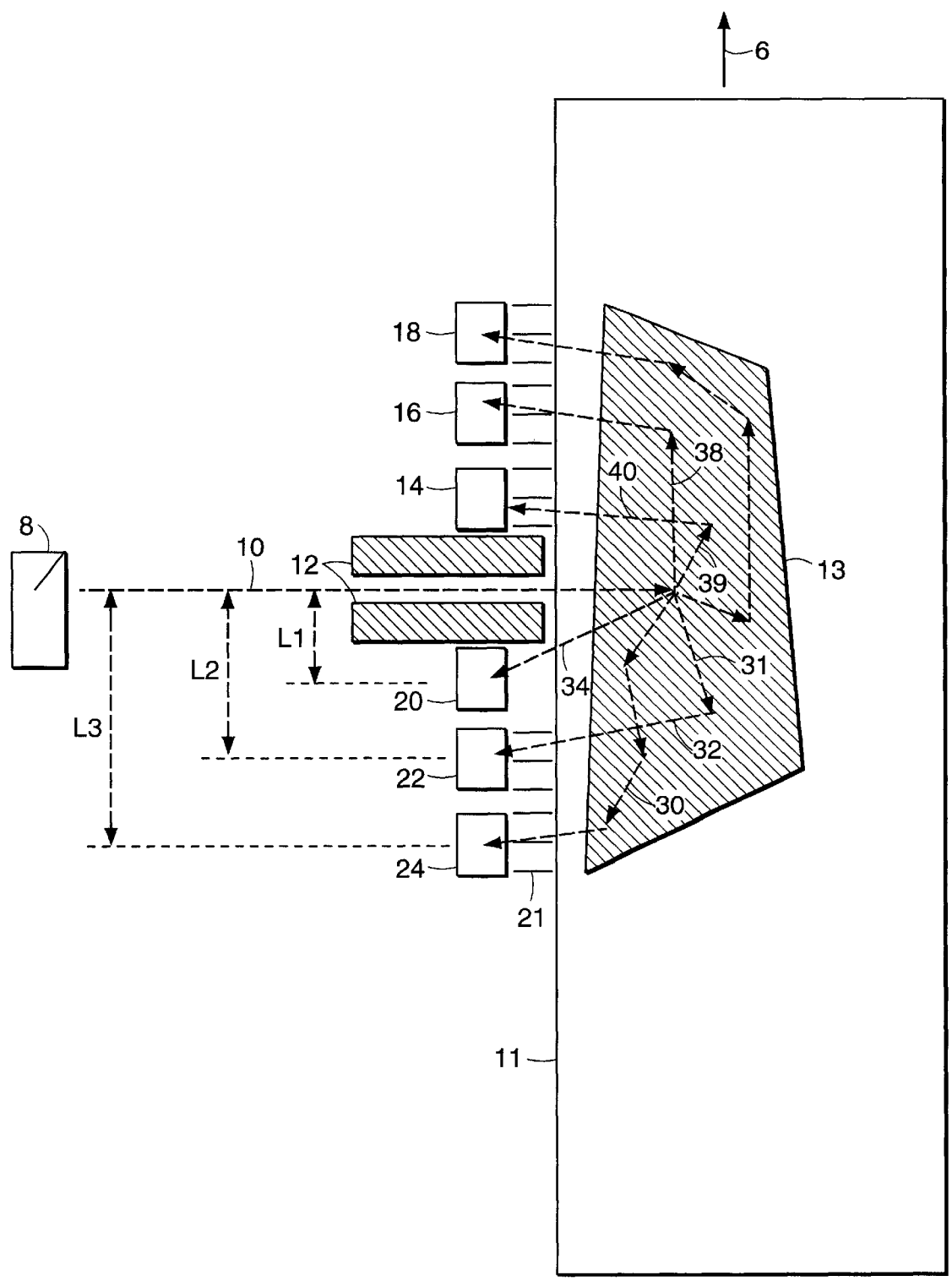
FIG. 1 provides a schematic representation of an x-ray system employing multiple backscatter detectors for measuring the density and atomic number of concealed objects in accordance with a preferred embodiment of the present invention.

X-rays 10 are scattered by the object 13, with several different x-ray scattering histories shown in FIG. 1. A single backscatter event is represented by scattered x-ray 34 going directly to backscatter detector 20. A double scattering is represented by incident x-ray 10, scattered once into scattered x-ray 39, and x-ray 39 scattered again, the resulting x-ray 40 entering detector 12, which is prevented from seeing single scattering events by collimators 21. A similar double scattering is shown as the sequence 10, 31, 32 into collimated detector 22. Sequences of 3 and 4 x-ray scatterings are also shown as 38 into collimated detector 18 and 30 into collimated detector 24.

Generally speaking, the intensity I(180°) of x-rays backscattered in a single scattering into the backward direction by an object of areal density d (density times thickness) and density ρ is proportional to the right-hand quantity in the expression:

$$I(180°) \propto \Omega_{inc}\Omega_{out}\left(\frac{\left(\frac{d\mu_{Comp}}{d\Omega}\right)_{180°}}{\mu_{inc} + \mu_{out}}\right)[1 - e^{-(\mu_{inc}+\mu_{out})d}]. \quad (1)$$

The sensitivity of Eqn. 1 to the effective atomic number Z of the object is contained in the term, in parentheses, which is the quotient of the differential mass absorption coefficient for Compton scatter through 180°, $(d\mu_{Comp}/d\Omega)_{180°}$, divided by the sum of the total mass absorption coefficient for the entering and exiting x-rays, $\mu_{inc}$ and $\mu_{out}$, respectively. The sensitivity of the quotient to the atomic number of the object increases rapidly as the x-ray energies drop below about 80 keV. But Eqn. 1 is also sensitive to other parameters: the geometrical factors, $\Omega_{inc}$ and $\Omega_{out}$, the solid angle factors from x-ray source 8 to object 13 and from the object to the backscatter detectors 20, respectively; the areal density d of object unless the areal density is great enough so that the exponential term can be neglected; and interposed material. The contribution of the interposed material, which has been omitted in Eqn. 1, can dominate the measured intensity and render the results completely insensitive to atomic number.

A scattering event of the sort described by Eqn. 1 is depicted in FIG. 1 by incident x-ray beam 10 being scattered by object 13 with the resulting backscattered x-ray 34 being detected by x-ray detector 20.

A more sensitive measure of the effective atomic number of the object is obtained when the backscatter intensity is restricted to those x-rays that have scattered more than once before being detected. This situation is illustrated in FIG. 1 by the double scattering 39/40 in which the incident x-ray beam 10 is scattered once in the material of object 13 and the resultant scattered x-ray 39 scatters again with result that x-ray 40 is counted in detector 14, which is shielded from direct scatterings by the thin collimators 21. The reason for the increased sensitivity is that the quotient term in Eqn. 1 enters more than once. For example, the measured intensity after a double scattering such as 39/40 will have the product:

$$I(180°) \propto \left(\frac{\left(\frac{d\mu_c^{inc}}{d\Omega}\right)_\theta}{\mu_{inc} + \mu_{scat1}} \frac{\left(\frac{d\mu_c^1}{d\Omega}\right)_\varphi}{\mu_{scat1} + \mu_{scat2}}\right)_{180°}, \quad (2)$$

where the first scattering through the angle θ, and the second scattering through the angle φ, are such that the final x-ray 40 enters detector 14. The second quotient is more sensitive to the effective atomic number than the first quotient, since the x-ray energies are lower. It should be appreciated that general analytic expressions for measured multiple scattering intensity in complex geometries are not available, but precise intensities are readily obtained by standard Monte Carlo codes of x-ray interactions.

The measured intensity in the collimated backscatter detector 14, while more sensitive to atomic number than that in detector 20, is still strongly dependent on geometric effects and the presence of interposed materials. Moreover, the measured intensity does not determine the density of the object 13.

Referring further to FIG. 1, in a preferred embodiment in which the invention is used for inspecting luggage, backscatter detectors such as 20, 22, and 24 are long detectors into the plane of FIG. 1. Container 11 may be luggage on a conveyor (not shown) moving in a direction 6 parallel to the array of backscatter detectors and the x-rays 10 may be in the form of a pencil beam that is rastered on container 11 in the plane perpendicular to the line of the detectors, including by the motion in direction 6. Other shapes of beam 10 may also be employed within the scope of the present invention. The invention may also be used to find explosives in land mines buried in the earth. A full inspection of the object 13 requires that x-ray beam 10 and object 13 be moved relative to each other. For example, an inspection for land mines requires that the x-ray source/detector system be moved across the earth face, while the inspection of luggage is most easily done by moving the luggage on a conveyer past the x-ray beam.

Referring further to FIG. 1, detector 20 is sensitive to x-rays that have scattered one or more times; it is, therefore, a conventional backscatter detector and it is sensitive to the effective atomic number of the object 13 as well as many confounding effects, however, alone, detector 20 is not sensitive to density. Detector 20 is shown a distance L1 from the axis of x-ray beam 10. A second backscatter detector 22 is shown a distance L2 from the intersection of the x-ray beam with the plane of the detectors and a third backscatter detector 24 is a distance L3 away from the axis of the x-ray beam. Both 22 and 24 are collimated so that they cannot see beam 10, thus they are not sensitive to direct single scattering.

The further the detector is disposed from the beam, the smaller is the measured backscatter intensity since further detectors have a decreased solid acceptance angle with respect to the x-ray beam and, additionally, the scattered x-rays are further attenuated due to increased path lengths within object 13. It is the decrease due to attenuation which produces an effect sensitive to the density of object 13. Detector 22 is a fixed distance, L1–L2, further from the beam than is detector 20. The intensity of backscatter radiation detected in detector 22 will be reduced from that detected in detector 20 by a term which, to some approximation, is proportional to $\exp[-\mu\rho(L2-L1)]$, where $\mu$ is the mass absorption coefficient. For x-ray energies greater than about 100 keV, the mass absorption coefficient is almost independent of the atomic number of the object so that the difference in intensities between detector 20 and detector 22 yields a measure of the density of the object.

The ratio of backscatter intensity detected by detector 22 to that detected by detector 20 is a more robust measure of density than that of the difference in detected intensities since, to a first approximation, the ratio is independent of the incident x-ray intensity and many geometrical effects. The ratio measure is also less sensitive than direct measures to the absorption due to intervening material.

Figure 2:
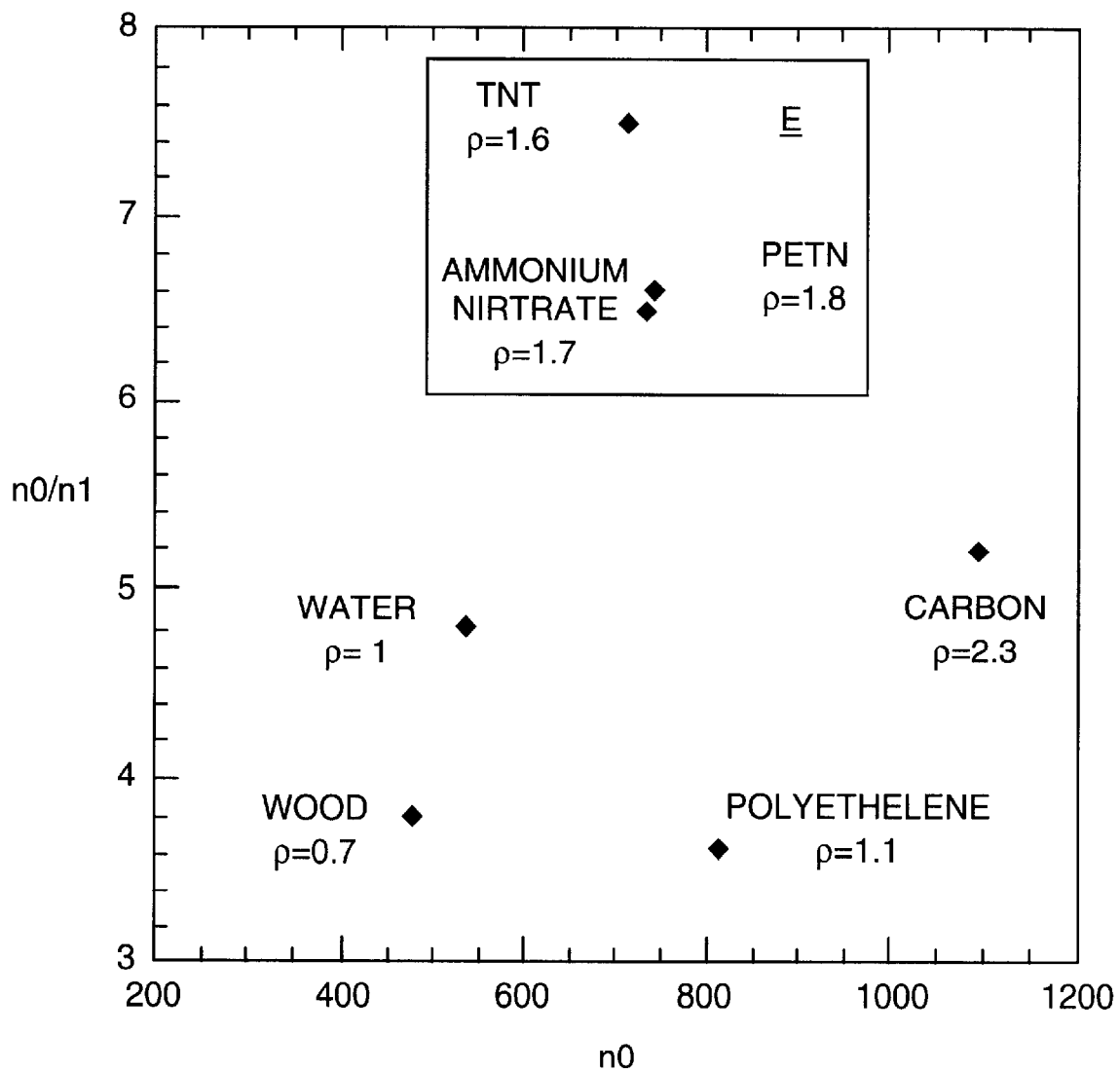
FIG. 2 shows a plot of simulated system sensitivity to various substances, with the ratio of counts in two detectors plotted against the number of counts in a single backscatter detector sensitive to singly scattered x-rays.

Computer simulations indicate that the ratio of counts in detector 22 to that in detector 20 yields as much information as does the ratio of counts in two collimated detectors such as 14 and 16, neither of which can detect single backscatter x-rays. Referring to FIG. 2, the quantity $n_0$ plotted along the horizontal axis is the number of counts detected by detector 20 sensitive to single backscatter x-rays. The quantity $n_1/n_0$ plotted along the vertical axis is the ratio of counts detected by offset detector 22 to the counts detected by detector 20.

The designated points on the plot show positions in the $n_0-n_1/n_0$ plane characteristic of various materials, the densities of which (in g/cm$^3$) are also shown. The bounded region E represents a region of potentially explosive, and therefore threatening, materials.

Figure 3:
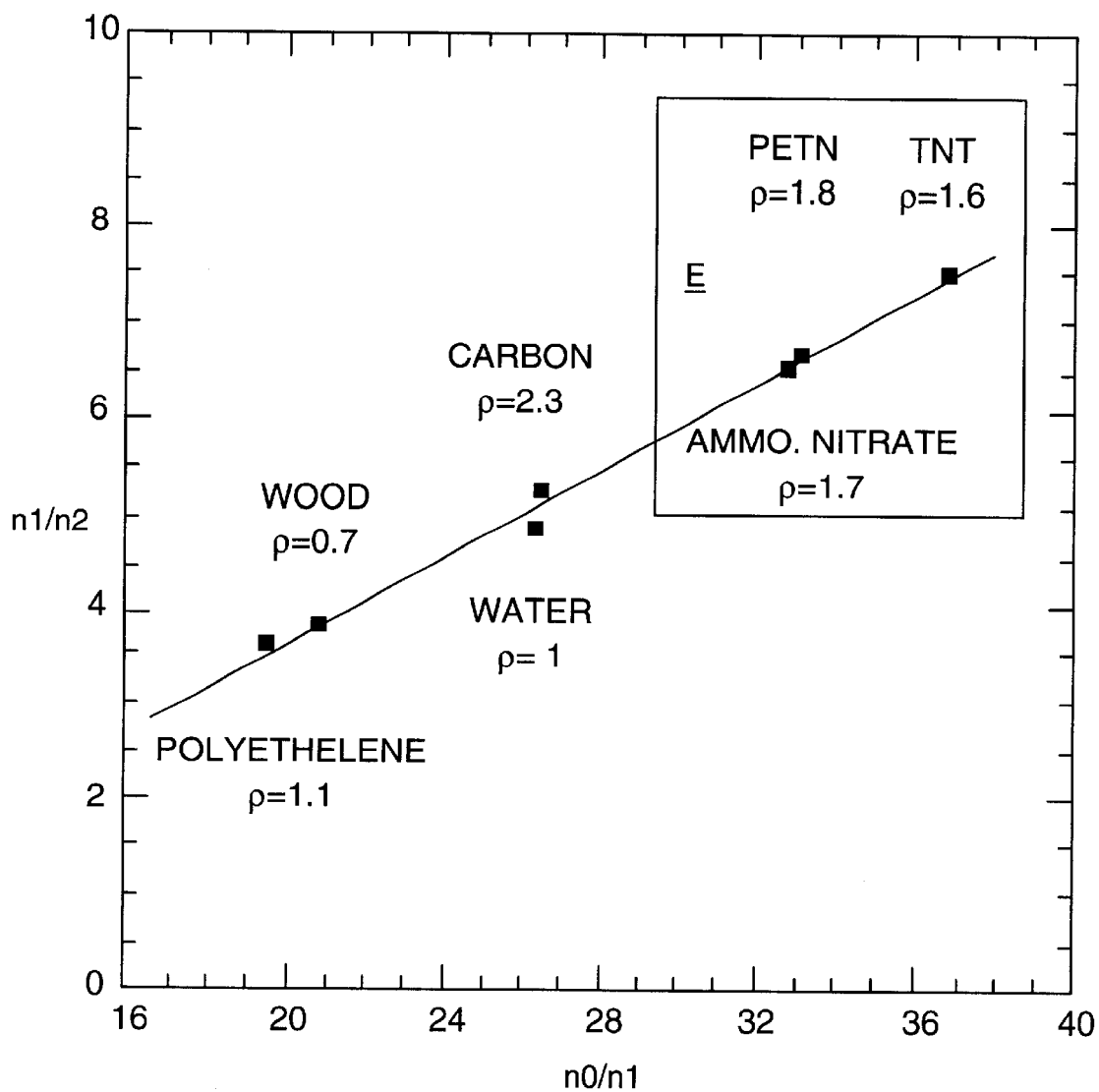
FIG. 3 shows a plot of simulated system sensitivity to various substances, with the ratio of counts in two multiple scatter detectors plotted against the ratio of counts in a multiple scatter detector to counts in a single backscatter detector sensitive to singly scattered x-rays.

Referring now to FIG. 3, computer simulations indicate that an even more discriminatory measure of the character of the object is obtained with three detectors such as 20, 22, and 24. With three detectors one has two independent ratios of detected intensities, and these are plotted, respectively, along the horizontal and vertical axes. and the phase space of the two ratios separates materials that have very similar effective atomic numbers but different densities, such as plastics and explosives, and materials with similar densities but different effective atomic numbers such as explosives and composites of plastics and metals. The discriminating power is shown by comparison of the simulation results presented in FIGS. 2 and 3.

In accordance with another embodiment of the invention, the selection of a signal based primarily on multiply scattered radiation as opposed to singly scattered radiation may be made spectrally, in addition to, or instead of, spatial separation as has been described. Since energy is lost at each Compton scattering, the less energetic backscattered photons are those that have been multiply scattered, especially if the source of radiation is initially monochromatic.

In accordance with other embodiments of the present invention, it is thus possible to simultaneously measure the effective atomic number of an object, using known techniques, as well as its density so as to give a more precise characterization of the object than can be obtained from each property alone. In some cases, it is possible to reduce or eliminate the effects of the objects geometry with respect to the x-ray source/detector arrangement as well as effects of interposed material.

It should be noted that the described embodiments of the invention may be used in combination of two or more of the above embodiments in order to inspect the contents of the container. The described embodiments of the invention are intended to be merely exemplary and numerous variations and modifications will be apparent to those skilled in the art. All such variations and modifications are intended to be within the scope of the present invention as defined in the appended claims.

We claim:

1. An inspection system for analyzing the density of an object which may be concealed within an enveloping surface, the system comprising:
   a. a source of penetrating radiation for emitting a beam having a propagation axis, the beam being incident upon the object;
   b. a first scatter detector for detecting penetrating radiation scattered at least one time within the object and for generating a first signal;
   c. a second scatter detector, having a field of view, for generating a second signal corresponding to penetrating radiation that has been multiply scattered within the object; and
   d. a controller for determining an effective density of the object on the basis of at least the first and second signals.

2. An inspection system according to claim 1, wherein the first scatter detector is disposed at a first distance measured on an orthogonal to the propagation axis of the beam and the second scatter detector is disposed at a second distance measured on an orthogonal to the propagation axis of the beam, the second distance being greater than the first distance.

3. An inspection system according to claim 1, further comprising at least one collimator for limiting the field of view of the second scatter detector to radiation that has been multiply scattered within the object.

4. An inspection system according to claim 1, wherein the second scatter detector is limited by spectral sensitivity from detecting penetrating radiation scattered fewer than twice by the object.

5. An inspection system according to claim 1, further comprising a third scatter detector for generating a third signal corresponding to penetrating radiation that has been multiply scattered within the object, such that the controller determines an effective density of the object on the basis of the first, second, and third signals.

6. An inspection system according to claim 1, wherein the source of penetrating radiation is an x-ray source.

7. An inspection system according to claim 1, wherein the source of penetrating radiation is a radioactive x-ray source.

8. An inspection system according to claim 1, further comprising a scanner for moving the propagation axis of the beam of penetrating radiation relative to the object.

9. A method for analyzing an object concealed within the ground, the method comprising:
   a. illuminating the ground with a beam of penetrating radiation;
   b. generating a first signal corresponding to penetrating radiation scattered at least one time within the object;
   c. generating a second signal corresponding to penetrating radiation that has been multiply scattered within the object; and
   d. determining an effective density of the object on the basis of at least the first and second signals.

10. A method for analyzing an object concealed within an enclosure, the method comprising:
   a. illuminating the enclosure with a beam of penetrating radiation;
   b. generating a first signal corresponding to penetrating radiation scattered at least one time within the object;
   c. generating a second signal corresponding to penetrating radiation that has been multiply scattered within the object; and
   d. determining an effective density of the object on the basis of at least the first and second signals.

* * * * *